United States Patent [19]

Swannie

[11] Patent Number: 4,762,409
[45] Date of Patent: Aug. 9, 1988

[54] LIGHT BULB UNIT FOR A SLIT LAMP

[76] Inventor: Mark K. Swannie, 1185 Stanton Ct., Colorado Springs, Colo. 80907

[21] Appl. No.: 849,117

[22] Filed: Apr. 7, 1986

[51] Int. Cl.⁴ .............................................. A61B 3/10
[52] U.S. Cl. .................................... 351/214; 351/221
[58] Field of Search ................ 351/214, 221; 313/113; 362/263, 293, 296, 310

[56] References Cited

U.S. PATENT DOCUMENTS

| | | |
|---|---|---|
| 3,068,745 | 12/1962 | Peck . |
| 3,405,994 | 10/1968 | Altman . |
| 3,407,019 | 10/1968 | Wilkinson . |
| 3,433,560 | 3/1969 | Gambs . |
| 3,467,466 | 9/1969 | Binstead . |
| 3,591,262 | 1/1969 | Gambs . |
| 3,652,153 | 3/1972 | Gambs . |
| 3,735,125 | 5/1973 | Wilms . |
| 3,749,481 | 7/1973 | Bosack . |
| 3,830,562 | 8/1974 | McGrann . |
| 3,944,343 | 3/1976 | Mueller . |
| 3,948,585 | 4/1976 | Heine . |
| 4,102,565 | 7/1978 | Takizawa . |
| 4,109,999 | 8/1978 | Kiyono . |
| 4,175,839 | 11/1979 | Muller . |
| 4,323,299 | 4/1982 | Roberts . |
| 4,331,392 | 5/1982 | Sato . |
| 4,357,079 | 11/1982 | Karasawa . |
| 4,396,260 | 8/1983 | Takizawa . |
| 4,411,502 | 10/1983 | Lang . |
| 4,456,348 | 6/1984 | Schulz . |
| 4,461,551 | 7/1984 | Blaha . |
| 4,504,129 | 3/1985 | Van Iderstine . |
| 4,509,106 | 4/1985 | Mayer et al. . |

Primary Examiner—Rodney B. Bovernick
Assistant Examiner—Jay Ryan
Attorney, Agent, or Firm—W. Scott Carson

[57] ABSTRACT

A removable and replaceable halogen light bulb unit for use in a slit lamp to examine the human eye. The unit includes a circular, disc-shaped base member to which a halogen bulb is mounted by support members. The unit further includes a reflector mounted between the base member and filament of the halogen bulb to reflect back into the slit lamp nearly all of the light which would otherwise pass upwardly and out of the slit lamp through the air holes.

23 Claims, 4 Drawing Sheets

U.S. Patent  Aug. 9, 1988  Sheet 2 of 4  4,762,409
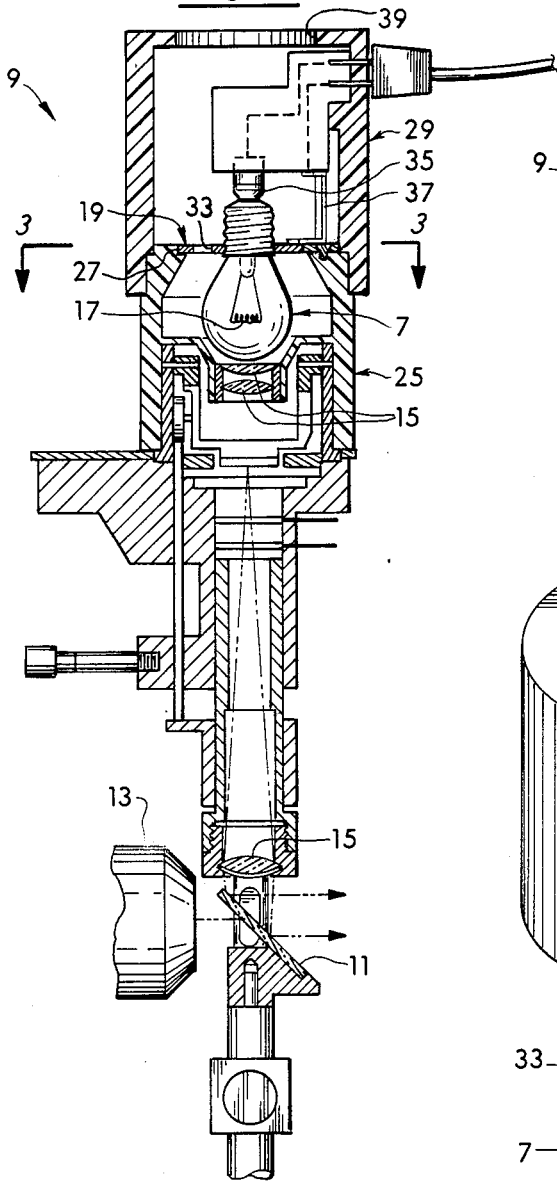
Fig. 2 (Prior Art)
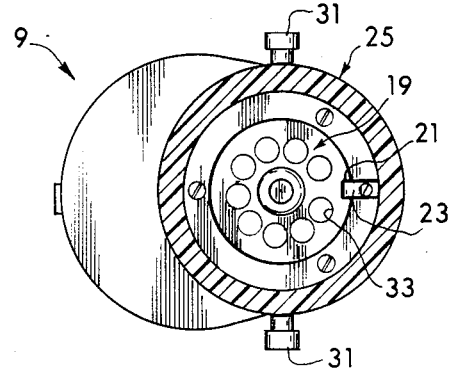
Fig. 3 (Prior Art)
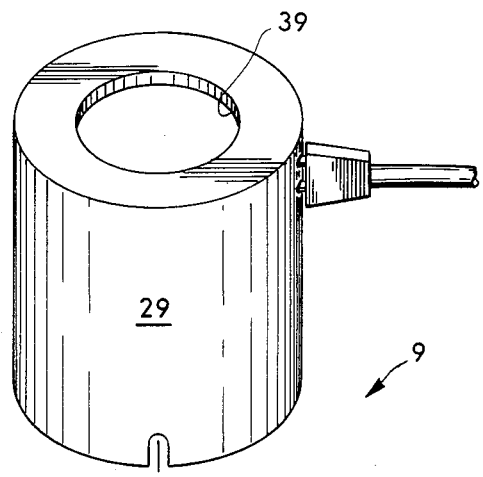
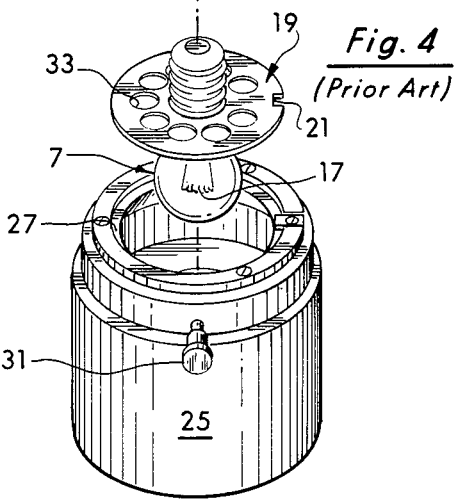
Fig. 4 (Prior Art)

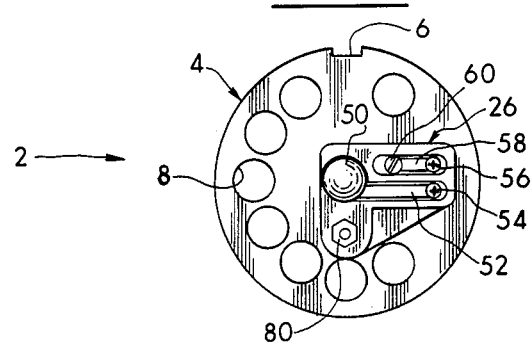
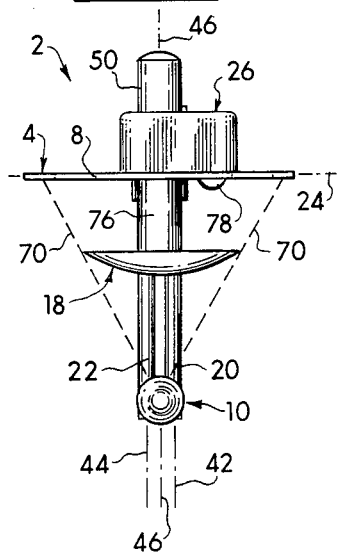
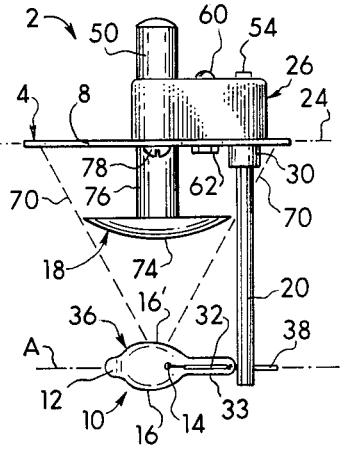
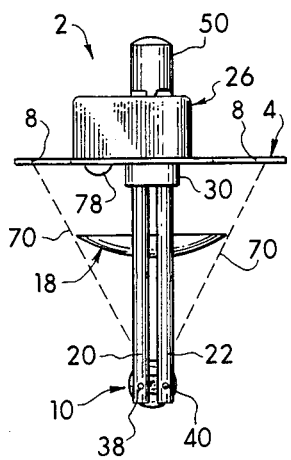
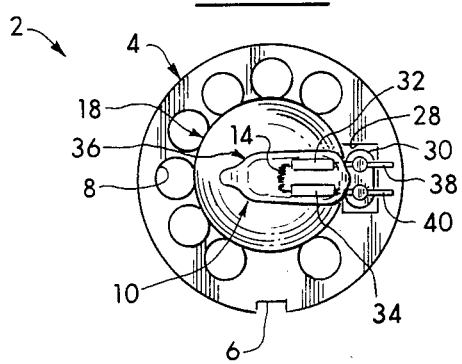

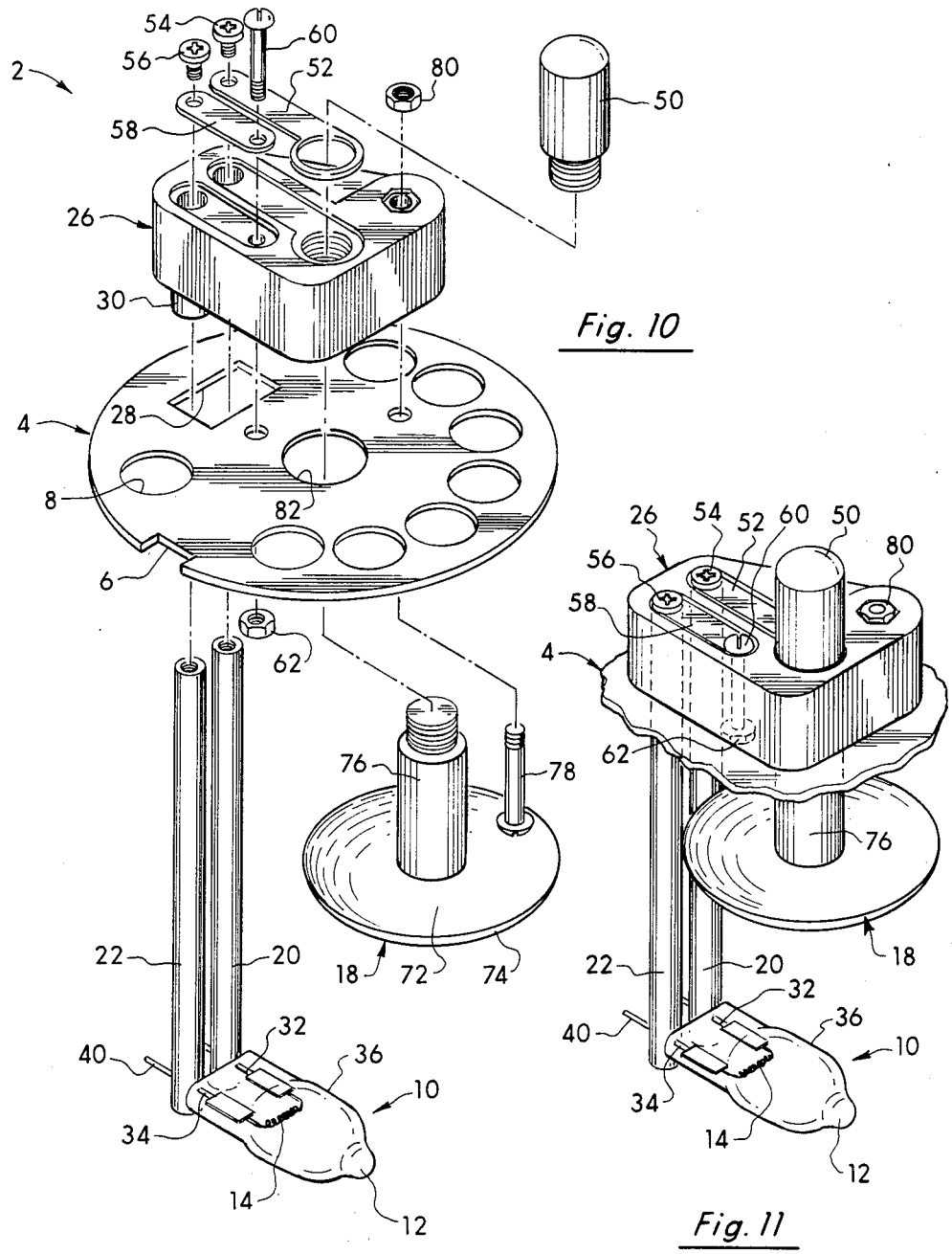

LIGHT BULB UNIT FOR A SLIT LAMP

BACKGROUND OF THE INVENTION

1. Field of the Invention

This invention relates to the field of removable and replaceable light bulb units for slit lamps.

2. Background Art

Slit lamps are widely used by ophthalmologists and optometrists to examine the human eye. In use, such lamps provide an illumination beam through a narrow slit which is then directed into the eye. The illumination beam is normally directed toward the eye along a horizontal axis and the slit lamp includes a microscope for examination by the operator of the area of the eye illuminated by the beam. To provide the beam and permit examination, the light source is commonly mounted to direct the light beam downwardly onto a mirror where it is then reflected horizontally into the eye. In operation, the light source or bulb is actually positioned upstream of one or more focusing lenses and must be precisely positioned within the slit lamp relative to these lenses both vertically and horizontally. Additionally, the filament of the light source or bulb must also be angularly oriented correctly about a vertical axis.

Various techniques have been used to properly position the light source or bulb within the slit lamp. Some techniques are more popular than others but they all strive to provide a simple and effective way to insert and replace the bulb without disturbing the alignment of the other operating members of the slit lamp. This is particularly important since burned out bulbs are usually removed and replaced by the ophthalmologist or optometrist himself or someone in his office.

In this regard, one of the most popular and widely used alignment techniques is to use a circular, disc-shaped base member to which an incandescent bulb is mounted. The circular base member abuts permanent structure in the slit lamp and not only serves to properly center the filament of the bulb horizontally (i.e., left and right relative to focusing lenses) but also vertically relative to the focusing lenses. Additionally, the circular perimeter of the base member is notched and cooperates with a locating pin on the slit lamp to correctly orient the filament of the bulb about a vertical axis. However, to date, this popular and effective technique using a circular base member has only been adapted to incandescent light bulbs wherein the base of the incandescent bulb fits directly into the circular base member. Incandescent bulbs have been used in slit lamps for years but their light tends to have a yellow tint at least in comparison with the almost pure white light of the more modern halogen bulbs. This yellow tint is highly undesirable in the examination of the human eye where true color is essential; yet, no design to date has been able to adapt a halogen bulb to a circular, disc-shaped base member so that it can be used as an original or replacement bulb in slit lamp models such as the Haag-Streit Model 900.

With this background, the present invention was developed. With the present invention, halogen bulbs can now be adapted for use with slit lamps built to receive circular, disc-shaped base members such as the Haag-Streit Model 900. Further, with the present invention, a reflector can additionally be used wherein nearly all of of the light emanating from the filament of the halogen bulb can be directed toward the eye under examination.

SUMMARY OF THE INVENTION

This invention involves a removable and replaceable light bulb unit for use in a slit lamp. The unit includes a circular, disc-shaped base member compatible with many of the more popular slit lamps including the Haag-Streit Model 900. The unit has an encapsulated, halogen light bulb mounted to the base member by a unique supporting and electrical arrangement. The arrangement includes two, cylindrical members which electrically connect the halogen bulb to the existing electrical system of the slit lamp. These members also support the filament of the halogen bulb at a precise, predetermined distance from the base member so that it will be properly positioned relative to the focusing lenses of the slit lamp upon its insertion into the lamp. Additionally, the present invention provides a light reflector mounted between the base member and the filament of the halogen bulb. With this addition, nearly all the light emanating from the filament toward the base member is reflected back into the slit lamp toward the eye being examined.

DESCRIPTION OF THE DRAWINGS

FIG. 2 is a cross-sectional view of the upper part or illumination column of the slit lamp of FIG. 1 showing the manner in which a common prior art light bulb is housed and its light directed downwardly onto a mirror to be relfected into the patient's eye.

FIG. 3 is a cross-sectional view taken along line 3—3 of FIG. 2 illustrating the manner in which the notched perimeter of the base member cooperates with a locating pin on the slit lamp to properly orient the filament of the bulb about a vertical axis.

FIG. 4 is an exploded view of the prior art light bulb of FIG. 2 and portions of its housing.

FIG. 5 is a side view of the removable and replaceable light bulb unit of the present invention.

FIG. 6 is a top view of the light bulb unit of the present invention taken from above FIG. 5.

FIG. 7 is a front view of the light bulb unit of the present invention taken from the left of FIG. 5.

FIG. 8 is a back view of the light bulb unit of the present invention taken from the right of FIG. 5 showing the orientation of the light bulb unit as it would appear in replacing the prior art, light bulb source of FIG. 2.

FIG. 9 is a bottom view of the light bulb unit of the present invention taken from below FIG. 5.

FIG. 10 is an exploded view of the light bulb unit of the present invention.

FIG. 11 is a perspective view of portions of the assembled light bulb unit of the present invention.

BEST MODES FOR CARRYING OUT THE INVENTION

Figure 1:
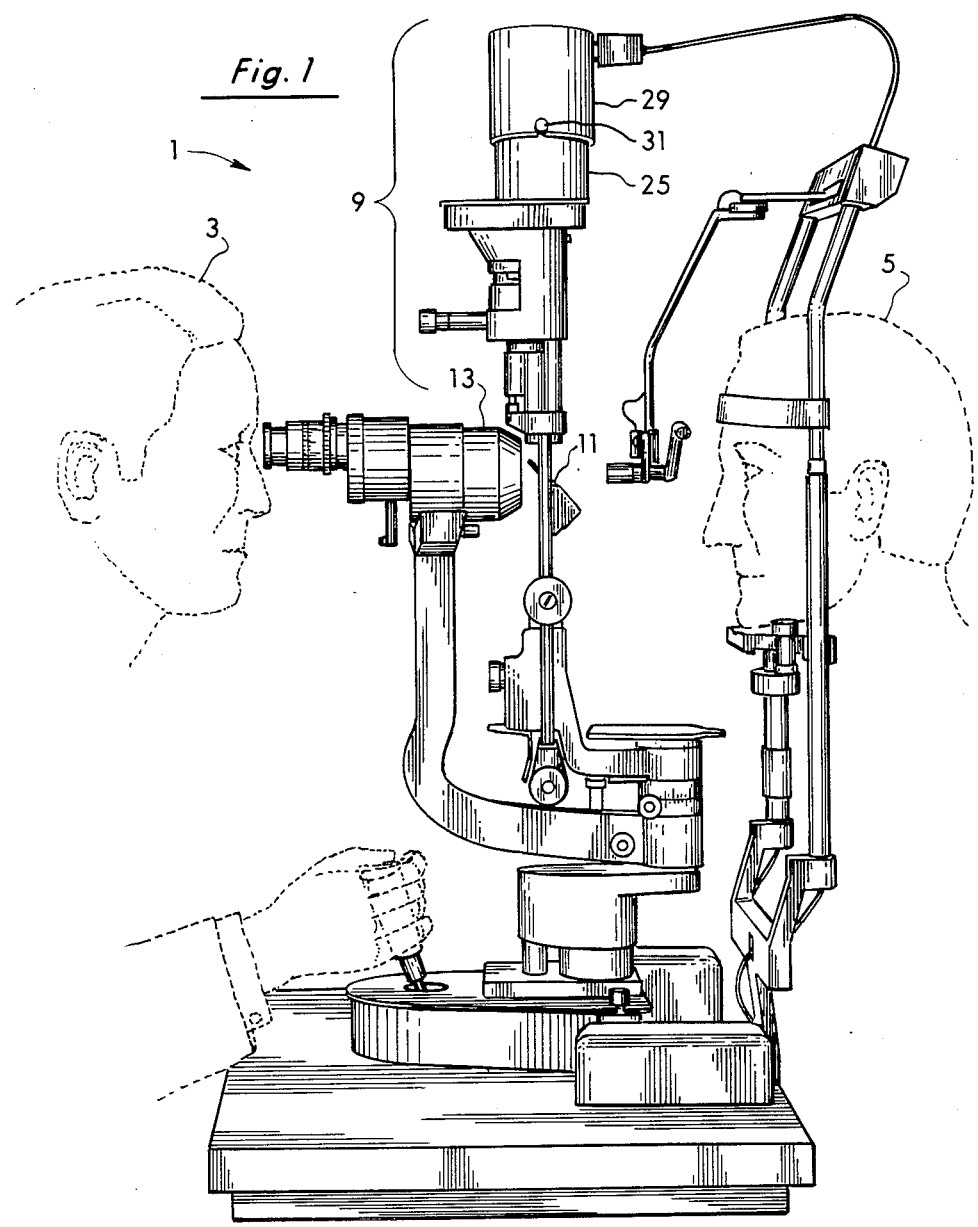
FIG. 1 illustrates a typical slit lamp design used by a doctor to examine a patient's eye.

As best seen in FIG. 1, slit lamps such as 1 are commonly used by ophthalmologists and optometrists to examine the human eye. In use, the doctor 3 and patient 5 sit opposite one another with the slit lamp 1 between them. An illumination beam is then generated by a light source such as the incandescent bulb 7 of FIG. 2 which is positioned in the upper part of illumination column 9 of slit lamp 1. The beam is directed downwardly where it is reflected off of the inclined mirror 11 (see FIG. 2) and into the eye of the patient 3 (see FIG. 1 and 2). The doctor 3 then examines the illuminated area of the eye through the microscope 13 which is part of the slit lamp 1.

The bulb 7 of FIG. 2 is acutally positioned upstream of one or more focusing lenses 15 and for proper operation, filament 17 of the light source or bulb 7 must be precisely positioned in the illumination column 9 relative to the focusing lenses 15 not only horizontally (i.e., left and right in FIG. 2) but also vertically (i.e., up and down in FIG. 2). Additionally, the filament 17 must be correctly oriented angularly about the vertical axis of the illumination column 9 so that the longitudinal axis of the filament 17 properly aligns with the inclined mirror 11.

These alignments can be done in a number of ways; however, a widely employed and popular technique is to use a circular, disc-shaped member 19 such as shown in the prior art illustrations of FIGS. 2-4. In operation, the incandescent bulb 7 is mounted to base member 19 with its filament 17 spaced a fixed and predetermined distance from the base member 19. The base member 19 is notched at 21 as best seen in Figure 4 and by aligning the notch 21 with locating pin 23 on the lamp housing 25 (see FIG. 3), the longitudinal axis of the filament 17 can be correctly oriented about the vertical axis of the housing 25. Additionally, with this circular, disc-shaped base member 19 received in the mating recess of ledge 27 in the housing 25 (see FIG. 2 and 4), the filament 17 of the bulb 7 can be precisely positioned both horizontally (i.e., left and right) vertically (i.e., up and down) relative to the focusing lenses 15 for proper operation of the slit lamp 1. This ease of positioning using the notched base member 19 is particularly popular with ophthalmologists and optometrists who often must replace their own bulbs 7 when they burn out. With this technique, they can easily and quickly do so without distrubing the operation of the other members of the slit lamp 1. In doing so, they merely have to remove the housing cap 29 by loosening the screws 31 (see FIGS. 3 and 4), lift out the burned out unit of bulb 7 with the attached base member 19, and insert a new unit of bulb 7 with attached base member 19, and then replace the housing cap 29. The arrangement of the aligning notch 21 and pin 23 and abutment of the base member 19 and recess 27 as illustrated in FIGS. 2 and 3 will then do all the work of correctly positioning the replacement bulb 7 in the housing 25.

Although the circular, disc-shaped base member 19 of FIGS. 2-4 is a very effective and popular alignment technique, it has not to date been adapted to handle a halogen bulb in the prior art environment of FIG. 2. In doing so, the incandescent bulb 7 of the prior art of FIG. 2 would be replaced with a more desirable halogen light source yet the basic design of the base member 19 would be maintained. Particular to the problem of such a replacement is that commonly available halogen bulbs of a desired size and operation are much smaller than the incandescent bulbs are of a different configuration (see the halogen bulb 10 of FIGS. 5 and 10) wherein the top or crown 12 (see FIG. 5) of the halogen bulb 10 is cloudy and the light from the filament 14 must pass through the clear sides 16 and 16' of the halogen bulb 10. Consequently, the halogen bulb 10 must be supported on its side. Further, the problem arises in adapting the halogen bulb 10 as a replacement for bulb 7 that the filament 14 of the halogen bulb 10 must be precisely positioned at the same distance from the base member 4 as the filament 17 of the incandescent bulb 7 of FIG. 2 is from its base member 19 for proper operation of slit lamp 1. Yet, with all these problems, the replacement of the incandescent bulb 7 with a halogen bulb 10 is highly desirable. That is, the halogen bulb 10 produces a much purer white light and its light does not have the characteristic yellow tint of an incandescent bulb. Such a yellow tint is very undesirable in the examination of the eye where true color is very important for proper examination and diagnosis of certain eye abnormalities and diseases.

With the above in mind, the halogen light bulb unit 2 of FIGS. 5-11 was developed to specifically replace the prior art incandescent light bulb 7 in the environment of slit lamp 1 of FIG. 2 without having to make any changes to the slit lamp 1 including its lamp housing 25 or cap 29. More specifically and referring to FIGS. 5-9, the halogen bulb unit 2 has a circular, disc-shaped base member 4 substantially similar to base member 19 of FIGS. 2-4. Like the base member 19, the base member 4 has a notch 6 in its perimeter and holes 8 to allow hot air to pass through it. However, unlike the prior unit of FIGS. 2-4, the light bulb unit 2 of the present invention has a halogen light bulb 10 and a dish-shaped reflector 18 mounted between the filament 14 of halogen bulb 10 and the base member 4. Additionally, the light bulb unit 2 of the present invention has two, cylindrical support members 20 and 22 mounted to the base member 4 which support the halogen bulb 10 on its side with its filament 14 precisely at the same predetermined distance from the plane 24 of the base member 4 as the incandescent filament 17 in FIG. 2 is from the corresponding plane of its base member 19. With the present invention, the filament 14 of the halogen bulb 10 can be precisely positioned in the exact location and orientation relative to the focusing lenses 15 as is the filament 17 of the prior art incandescent bulb 7 illustrated in FIG. 2.

Referring again to FIGS. 5 and 10, the cylindrical support members 20 and 22 are mounted to the base member 4 by the mounting block 26. The support members 20 and 22 and base member 4 are all electrically conducting members; however, the mounting block 26 is preferably made of plastic and is non-conducting. Further, as best seen in FIGS. 8 and 10, although the first or upper end portions of the support members 20 and 22 pass through the rectangular slot 28 (see FIG. 10) in the base member 4, the support members 20 and 22 are electrically insulated from the base member 4. This is accomplished by portion 30 (see FIGS. 8 and 10) of the mounting block 26 which portion 30 extends through the rectangular slot 28 in the base member 4 and is positioned not only between the support members 20 and 22˙ themselves but also between each support member 20 and 22 and base member 4. In this manner, the support members 20 and 22 pass through the base member 4 but are electrically insulated from each other and the base member 4.

The halogen light bulb 10 as best seen in FIGS. 5, 9, and 10 has a filament 14 and first and second electrode members 32 and 34 attached to it. The filament 14 and attached electrode members 32 and 34 substantially lie in a common plane (see FIGS. 5 and 9). The bulb 36 (see FIGS. 5 and 9) serves to encapsulate filament 14 and first end portions of the electrode members 32 and 34 leaving the second end portions 38 and 40 of the electrode members 32 and 34 extending outwardly of the bulb 36. In the preferred embodiment as illustrated in FIG. 8-11, the outwardly extending, second end portions 38 and 40 of the electrode members 32 and 34 are received in holes in the second or lower end portions of the support members 20 and 22. In this manner, the halogen bulb 10 is then supported with its filament 14 at a fixed, predetermined distance from the plane 24 of the base member 4 (see FIG. 5) with the filament 14 and the electrode members 32 and 34 all in a common plane substantially parallel to the plane 24 of the base member 4 and with the axis A between the top 12 and bottom 33 of the bulb 10 parallel to the plane 24. Additionally, as best seen in FIG. 7, the support members 20 and 22 which are mounted by the mounting block 26 with the axies 42 and 44 spaced from and substantially parallel to the central axis 46 of the base member 4. The axes 42 and 44 are also substantially perpendicular to the plane 24 of the base member 4 and the support members 20 and 22 and their axes 44 and 46 all lie within the projected perimeter of the base member 4 (i.e., they do not extend radially beyond the perimeter of the base member 4 as viewed from above or below in FIGS. 6 and 9).

The base member 4, support members 20 and 22, electrode members 32 and 34 and filament 14 are all made of metal and are electrically conducting members. In operation, as best seen in FIG. 11, these members provide a flow path for electricity from the electrical contact 50 to the metallic bridge 52, screw 54, first support member 20, first electrode member 32, filament 14, second electrode member 34, support member 22, screw 56, metallic bridge 58, screw-nut arrangement 60 and 62, and base member 4. In this manner and with the light bulb unit 2 of the present invention in the environment of FIG. 2, electricity will flow through the filament 14 when an electrical potential is applied between or across the electrical contacts 35 and 37 in FIG. 2. Additionally, current will flow through any segment of this circuit (e.g., from the first support member 20 to the first electrode member 32 to the filament 14 to the second electrode member 34 to the second support member 22 and to the base member 4 through the screw 56, metallic bridge 58 and screw-cut arrangement 60 and 62) when an electrical potential is applied between or across the segment.

The light bulb unit 2 of the present invention preferably also includes the light reflector 18 which is mounted between the filament 14 of the halogen bulb 10 and the base member 4 (see FIG. 5). The purpose of the reflector 18 is to reflect light that would otherwise pass upwardly through the hot air holes 8 in the base member 4 and be wasted. More specifically, the base member 4 has a series of holes 8 about its central axis 46 within the perimeter of the base member 4 as shown in FIG. 6. The purpose of these holes 8 is to allow air to circulate about the bulb 10 in the illumination column 9 of FIG. 2 with the hot air rising through the holes 8 in the base member 4 and out the central hole 39 in the cap (see FIGS. 2 and 4). This circulating air helps keep the bulb 7 or 10 from overheating. In the prior art incandescent bulb 7 of FIG. 2, the corresponding holes 33 not only allow air to pass out but also allow the upwardly directed light to wastefully pass out of the slit lamp 1. This loss of illumination often causes the operator of slit lamp 1 of FIG. 2 to increase the voltage and current through the prior art bulb 7 in order to achieve the desired illumination; and, this increase often leads to early burn out of the incandescent bulb 7. In contrast, the preferred embodiment of FIGS. 5-11 includes the reflector 18 which as shown by lines 70 in FIG. 5, 7, and 8, reflects back nearly all, if not all, of the light emanating upwardly from the filament 14 from the bulb side 16' toward the holes 8 in the base member 4. Further, it does so without adversely affecting the circulation of air through the holes 8.

As illustrated, the reflector 18 is preferably dish-shaped with concave and convex sides 72 and 74 (see FIG. 10) with the convex side 74 (see FIG. 5) preferably mounted to face the filament 14 of halogen bulb 10. The axis of the reflector 18 is preferably colinear with the central axis 46 of the base member 4 and the radius of the reflector 18 is preferably less than the distance between the central axis 46 of the base member 4 and the support members 20 and 22 so that the reflector 18 does not physically touch the support members 20 and 22. Additionally, the mounting block 46 for the reflector 18 mounts the reflector 18 to the base member 4 in a non-conducting manner. That is, the reflector 18 has a stem 76 attached to it as best seen in FIG. 10. The stem 76 is threaded at one end and screws into the mounting block 26 which in turn is fixed to the base member 4 by the screw-nut arrangements 60 and 62 and 78 and 80. The central hole 82 in the base member 4 is preferably larger than the diameter of the stem 76 so that in the assembled position, the stem 76 is spaced and electrically insulated from the base member 4. The stem 76 is also spaced from and electrically insulated from a corresponding stem of electrical contact member 50.

As discussed above, the base member 4 is totally compatible with the housing 25 of the prior art slit lamp of FIGS. 2-4 wherein the halogen light bulb unit 2 of the present invention can be easily and quickly substituted as a unit for the prior art light source of base member 19 and incandescent bulb 7 in the slit lamp 1 of FIGS. 1-4. Consequently, with the present invention, a halogen light source can now be adapted for use in the slit lamp 1 of FIGS. 1-4 without making any structured changes to the slit lamp 1 including its housing 25 or cap 29.

While several embodiments of the present invention have been shown and described in detail, it is to be understood that various modifications could be made to these embodiments without departing from the scope of the invention.

I claim:

1. A light bulb unit primarily intended for use in a slit lamp for examining eyes, said unit including:

a substantially circular, disc-shaped base member extending about a central axis substantially in a plane, first and second support members, each of said support members being elongated and having first and second end portions spaced from each other, and means for mounting said first and second support members to said base member with the second end portions of each respective support member spaced from said base member, an encapsulated light bulb, said light bulb having a filament, first and second electrode members attached to said filament, and bulb means for encapsulating said filament and a first portion of each of said first and second electrode members, each of said electrode members having a second portion extending outwardly of said bulb means, means for mounting the second portion of said first electrode member to the second portion of said first support member and means for mounting the second portion of said second electrode member to the second portion of said second support member whereby said encapsulated light bulb is supported on said base member with the filament thereof at a predetermined distance from the base member, and, a light reflector having a convex side and means for mounting said light reflector between said filament and said base member with said convex side thereof facing said filament wherein light emanating from said filament toward said base member is substantially reflected away from said base member.

2. The light bulb unit of claim 1 wherein the first and second support members extend along respective first and second axes and said mounting means for said support members mounts said first and second support members to said base member with the first and second axes spaced from the central axis of the base member.

3. The light bulb unit of claim 2 wherein the mounting means for said support members mounts said first and second support members to said base member with the first and second axes substantially parallel to the central axis of the base member.

4. A light bulb unit primarily intended for use in a slit lamp for examining eyes, said unit including:

a substantially circular, disc-shaped base member extending about a central axis substantially in a plane, first and second support members, each of said support members being elongated and having first and second end portions spaced from each other, and means for mounting said first and second support members to said base member with the second end portions of each respective support member spaced from said base member, an encapsulated light bulb, said light bulb having a filament, first and second electrode members attached to said filament, and bulb means for encapsulating said filament and a first portion of each of said first and second electrode members, each of said electrode members having a second portion extending outwardly of said bulb means, means for mounting the second portion of said first electrode member to the second portion of said first support member and means for mounting the second portion of said second electrode member to the second portion of said second support member whereby said encapsulated light bulb is supported on said base member with the filament thereof at a predetermined distance from the base member, and, a light reflector and means for mounting said light reflector between said filament and said base member wherein light emanating from said filament toward said base member is substantially reflected away from said base member and wherein said first and second support members are respectively mounted to said base member at first and second distances from the central axis of the base member and said light reflector sxtends outwardly of said central axis for a distance less than the smaller of the first and second distances.

5. The light bulb unit of claim 4 wherein the base member, support members, electrode members, and filament are all electrically conducting members and said light bulb unit includes means for providing a flow path for electricity through the first support member to the first electrode member to the filament to the second electrode member to the second support member and to the base member when an electrical potential is applied between the first support member and the base member.

6. The light bulb unit of claim 4 wherein the filament and first and second electrode members of the encapsulated light bulb extend substantially in a common plane substantially parallel to the plane of the base member.

7. The light bulb unit of claim 4 wherein the first and second support members extend along respective first and second axes and said mounting means for said support members mounts said first and second support members to said base member with the first and second axes substantially parallel to the central axis of the base member.

8. The light bulb unit of claim 7 wherein the circular base member has a perimeter extending about the central axis substantially at a first radius and each of said first and second axes of said support members extends substantially parallel to the central axis at a distance from said central axis less than said first radius.

9. The light bulb unit of claim 4 wherein each of the support members is substantially cylindrical.

10. The light bulb unit of claim 4 wherein at least one of the support members passes through the base member.

11. The light bulb unit of claim 4 wherein both of said support members pass through the base member.

12. The light bulb unit of claim 4 wherein said support members and base member are electrically conducting members and said mounting means for said support members includes means to electrically insulate one of the support members from said base member.

13. The light bulb unit of claim 11 further including means to electrically couple the other of said support members to said base member.

14. The light bulb unit of claim 4 wherein said support members and base member are electrically conducting members and said light bulb unit includes means to electrically couple one of said support members to said base member.

15. The light bulb unit of claim 4 wherein said encapsulated light bulb is a halogen bulb.

16. The light bulb unit of claim 4 wherein said base member has a series of holes therethrough to allow air to pass through the base member.

17. The light bulb unit of claim 16 wherein said circular base member has a perimeter extending about the central axis substantially at a first distance and said series of holes are located within said perimeter whereby air can pass through the base member within the perimeter thereof.

18. The light bulb unit of claim 16 wherein said series of holes extend substantially about the central axis of said base member.

19. The light bulb unit of claim 4 wherein the base member has a perimeter with at least one inwardly extending notch therein.

20. The light bulb unit of claim 4 wherein said mounting means for said light reflector mounts said light reflector to said base member.

21. The light bulb unit of claim 4 wherein said base member has a series of holes therethrough to allow air to pass through the base member and said reflector reflects light emanating from said filament toward the holes in said base away from said holes.

22. A light bulb unit primarily intended for use in a slit lamp for examining eyes. said unit including:

a substantially circular, disc-shaped base member extending about a central axis substantially in a plane, an encapsulated halogen light bulb, said light bulb having a filament, first and second electrode members attached to said filament, and bulb means for encapsulating said filament and a first portion of each of said first and second electrode members, each of said electrode members having a second portion extending outwardly of said bulb means, means for respectively mounting the second portions of said first and second electrode members to the circular, disc-shaped base member whereby said encapsulated light bulb is supported on said base member with the filament thereof at a predetermined distance from the base member, and, a light reflector and means to mount said light reflector between said filament and said base member wherein said light reflector has a convex side and said mounting means for said light reflector mounts the light reflector with the convex side thereof facing said filament so that light emanating from said filament toward said base member is substantially reflected away from said base member by said reflector.

23. A light bulb unit primarily intended for use in slit lamp for examining eyes, said unit including:

a substantially circular, disc-shaped base member extending about a central axis substantially in a plane, an encapsulated halogen light bulb, said light bulb having a filament, first and second electrode members attached to said filament, and bulb means for encapsulating said filament and a first portion of each of said first and second electrode members, each of said electrode members having a second portion extending outwardly of said bulb means at the bottom of said bulb means, said bulb means having a cloudy, top spaced from the bottom of said bulb means in a first direction along an axis and clear sides extending substantially between said top and bottom, said filament and said first and second electrode members extending substantially in a common plane, and, means for respectively mounting the second portions of said firt and second electrode members tot he circular, disc-shaped base member whereby said encapsulated light bulb is supported on said base member with the filament thereof at a predetermined distance from the base member with the common plane of said filament and said first and second electrode members spaced from and substantially parallel to the plane of the base member and with said axis between said top and bottom of said bulb means also spaced from and substantially parallel to the plane of said base member wherein said bulb means is sideways relative to the plane of said base member so that light emanating from the filament toward and away from the plane of said base member passes through the clear sides of the bulb means rather than through the bottom and cloudy top of the bulb means.

* * * * *